United States Patent

Beck et al.

[11] 4,018,784
[45] Apr. 19, 1977

[54] PREPARATION OF TRICHLOROTHIAZOLE AND INTERMEDIATE

[75] Inventors: Günther Beck, Leverkusen; Hans Holtschmidt, Berg.Gladbach, both of Germany

[73] Assignee: Bayer Aktiengesellschaft, Leverkusen, Germany

[22] Filed: Dec. 9, 1975

[21] Appl. No.: 639,136

[30] Foreign Application Priority Data

Dec. 12, 1974 Germany .......................... 2458824

[52] U.S. Cl. ...................... 260/302 R; 260/566 D
[51] Int. Cl.² ...................................... C07D 277/32
[58] Field of Search ................... 260/566 D, 302 R

[56] References Cited
UNITED STATES PATENTS 3,190,918   6/1965   Holtschmidt ................ 260/566 D
3,674,829   7/1972   Arlt ............................. 260/566 D Primary Examiner—Richard J. Gallagher
Attorney, Agent, or Firm—Burgess, Dinklage & Sprung

[57] ABSTRACT

Trichlorothiazole of the formula

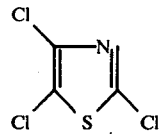

is prepared by reacting 1,2,2,2-tetrachloroethylisocyanidedichloride of the formula

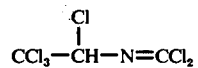

with 1 to 1.2 times the stoichiometric amount of sulfur at a temperature of about 150° to 250° C, preferably about 170° to 230° C.

7 Claims, No Drawings

PREPARATION OF TRICHLOROTHIAZOLE AND INTERMEDIATE

The invention relates to a new process for the preparation of trichlorothiazole.

A process for the preparation of trichlorothiazole has been disclosed in U.S. Pat. No. 3,833,601 (= German Published Specification 2,213,865). The starting compounds used therein, namely pentachloroethyl-isocyanide-dichloride or trichlorovinyl-isocyanide-dichloride, can only be prepared in low yield and/or by multi-stage synthesis. A further disadvantage of this process is that considerably amounts of disulfur dichloride arise as an undesired by-product.

It has been found that trichlorothiazole of the formula

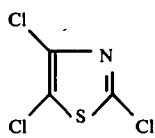  (I)

is obtained when 1,2,2,2-tetrachloroethyl-isocyanide-dichloride of the formula

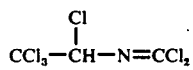  (II)

is reacted with sulfur in the temperature range of about 150° to 250° C. Preferably, the reaction is carried out in the temperature range of about 170° to 230° C.

The process of the invention is explained in more detail by the following equation:

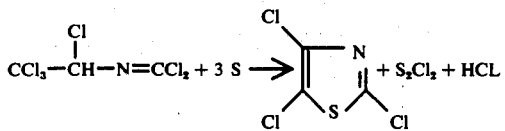

In general, in the process according to the invention, at least 3 moles of sulfur are employed per mole of starting compound (II) in order to achieve as complete conversion to (I) as possible; suitably, for example, up to about 20% excess of sulfur can be used. Preferably, an amount which ranges from about the stoichiometrically required amount of sulfur to about 1.2 times this amount is employed for the reaction.

1,2,2,2-Tetrachloroethyl-isocyanide-dichloride of the formula (II), used as the starting material, was not previously known. It is prepared, as is described in detail in the experimental section, from chloral-formamide (Ber. dtsch. chem. Ges. 45, 945) by reaction with chlorine and a highly active inorganic acid chloride, such as phosphorus pentachloride or a mixture of phosphorus trichloride and at least an equimolar amount of chlorine, or thionylchloride containing an addition of about 0.01 to 10% by volume of a lower alkyl substituted amide of a lower aliphatic carboxylic acid such as dimethylformamide, in accordance with the equation:

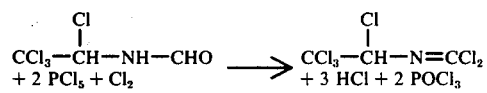

in about 90% yield.

From the equation follows that the requisite amounts of acid chloride and chlorine are at least 2 moles of acid chloride and 1 mole of chlorine per mole of chloralformamide. The acid chlorides are generally applied in amounts of 2 to 2.3 mole per mole of chloralformamide. Chlorine is preferably used in an excess over the stoichiometrical amount of 1 mole per mole chloralformamide, the excess being such that the waste gases of the reaction are colored greenish.

To carry out the process of the invention it is possible, for example, to mix the starting compound of the formula (II) - suitably with exclusion of moisture, with about 3 to 3.5 moles of sulfur per mole of (II) and heat the mixture to the stated reaction temperature, preferably about 170°–230° C. After an initial evolution of hydrogen chloride gas between 190° to 200° C has subsided, the mixture is heated under reflux until the absorption between 1,600 to 1,650 cm$^{-1}$ which is characteristic of all isocyanide-dichlorides has disappeared in the IR spectrum of the reaction mixture. In order to be able to keep the reaction temperature to the requisite level and in order thereby to achieve as complete conversion as possible, it is advisable continuously to distil off the disulfur dichloride (in addition to very small proportions of sulfur dichloride, formed during the reaction according to equation (1). To prevent unconverted starting material distilling with the sulfur chlorides produced, it is advantageous to interpose a column. A first indication of the end of the reaction is provided by the fact that no more sulfur chlorides distil over. Of course, the process can also be carried out continuously.

Trichlorothiazole of the formula (I) is known from U.S. Pat. No. 3,833,601 and exhibits insecticidal properties.

Compared to the processes of preparation of trichlorothiazole (I) according to U.S. Pat. No. 3,833,601 the process according to the invention has the advantage that it starts from 1,2,2,2-tetrachloroethyl-isocyanide-dichloride as an easily accessible starting compound and that the production of disulfur dichloride is reduced to half compared to the process according to German Published Specification 2,213,865, which starts from pentachloroethyl-isocyanide-dichloride.

EXAMPLE a. Preparation of the starting material

In the course of about 2.5 hours, 330 g (2.4 moles) of phosphorus trichloride are added dropwise to a suspension, kept at 20° to 30° C by cooling with ice and saturated with chlorine, of 200 g (1.04 moles) of chloralformamide in 200 ml of carbon tetrachloride. Thereafter the temperature is raised to the reflux point (about 95° C) over the course of about one hour while continuing to pass in excess chlorine (recognizable from the greenish color of the off-gas). After replacing the reflux condenser by a distillation bridge, the mixture is heated, in the course of about 3 hours, to about 150° C while continuously distilling off carbon tetrachloride, and phosphorus oxychloride formed, in the stream of chlorine. After passing in sulfur dioxide for about half an hour until the excess phosphorus pentachloride has been destroyed, at between 120° and 130° C, the mix-mixture is distilled under a waterpump vacuum. At 15 mm Hg, starting with material passing over at 92° C and continuing to a bath temperature of about 200° C, 239 g of distillate are obtained, containing, according to analysis by gas chromatography, 232 g (corresponding to 84.5% of theory) of 1,2,2,2-tetrachloroethyl-isocyanide-dichloride of the formula

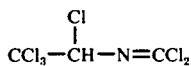

According to analysis by gas chromatography, the first runnings which distil off in the stream of chlorine or in the stream of SO₂ contain a further 7 g. Accordingly, the total yield of 1,2,2,2-tetrachloroethyl-isocyanide-dichloride is 87% of theory. A purity of more than 99.5%, according to gas chromatography, is achieved by fractional distillation using an approximately 80 cm Vigreux column with dephlegmator. Boiling point 95° C/12 mm Hg. The empirical formula $C_3HCl_6N$ is confirmed by the mass spectrum. The compound shows a characteristic IR spectrum with the following main bands (in cm⁻¹): 1,634, 1,305, 1,019, 918, 825, 751 and 577.

¹H-NMR spectrum (without solvent): = 5.75 ppm, relative to TMS.

b. 132 g (0.5 mole) of 1,2,2,2-tetrachloroethyl-isocyanide-dichloride of the formula

are heated with 56 g (1.75 moles) of sulfur, while excluding moisture, in a three-necked flask equipped with a stirrer, thermometer and about 60 cm long Vigreux column with dephlegmator. A distinct evolution of hydrogen chloride gas can be observed at about 195°–205° C. When this has subsided, the bath temperature is raised from initially 220° – 230° C to 250° – 260° C, in the course of which the internal temperature initially rises to a maximum value of about 216° to 218° C (after about 12 hours from the beginning of the reaction) and then drops to about 206°–208° C. During the reaction, the sulfur chlorides produced (very predominantly $S_2Cl_2$, with small proportions of $SCl_2$) largely distil off through the column. The end of the reaction is first indicated by the fact that no further sulfur chlorides distil over. An even more reliable determination of the end point is provided by IR samples of the reaction mixture: 100% conversion is reached when the very strong IR band at between 1,600 and 1,650 cm⁻¹ which is characteristic of all isocyanide-dichlorides has disappeared. The total time required for this is about 40 hours; after about 20 hours the conversion is, as may be seen from the IR spectrum, already about 70 – 80%. After completion of the reaction, distillable material is first thoroughly removed, under a waterpump vacuum, through a bridge, until the bath temperature is about 250° C, and the distillate is then again fractionated using a column. At boiling point 76°–78° C/12 mm Hg, 71 g (corresponding to 75% of theory) of pure trichlorothiazole of the the formula

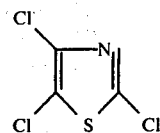

are obtained; the material corresponds in all its properties to that obtained according to U.S. Pat. No. 3,833,601.

If desired, the intermediate 1,2,2,2-tetrachloroethyl-isocyanide-dichloride need not be isolated and/or purified before proceeding to employ it in the reaction with sulfur. Instead, the reaction solution with little or no purification can be directly employed in the reaction with sulfur.

What is claimed is

1. A process for the preparation of trichlorothiazole of the formula

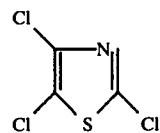

comprising reacting 1,2,2,2-tetrachloroethyl-isocyanide-dichloride of the formula

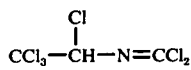

with sulfur at a temperature of about 150° to 250° C.

2. The process according to claim 1, wherein the reaction is carried out at a temperature of about 170° to 230° C.

3. The process according to claim 1, wherein the reaction is carried out with about 1 to 1.2 times the stoichiometric amount of sulfur.

4. 1,2,2,2-tetrachloroethyl-isocyanide-dichloride of the formula

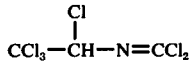

5. The process for making 1,2,2,2-tetrachloroethyl-isocyanide-dichloride according to claim 4, which comprises reacting chloral-formamide with chlorine and a highly active inorganic acid chloride.

6. The process according to claim 5 wherein the highly active inorganic acid chloride is phosphorus pentachloride or a mixture of phosphorus trichloride and at least an equimolar amount of chlorine or thionylchloride containing an addition of 0.01 to 10% by volume of a lower alkyl substituted acid of a lower aliphatic carboxylic acid.

7. The process according to claim 5, including the further steps of adding sulfur dioxide to destroy any unconsumed phosphorus chlorides and then distilling to separate impurities.

* * * * *